United States Patent
Allgeier et al.

(10) Patent No.: US 11,376,223 B2
(45) Date of Patent: Jul. 5, 2022

(54) PHARMACEUTICAL COMPOSITIONS

(71) Applicant: Eli Lilly and Company, Indianapolis, IN (US)

(72) Inventors: Matthew Carl Allgeier, Fishers, IN (US); Tony Yantao Zhang, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 113 days.

(21) Appl. No.: 16/628,101

(22) PCT Filed: Jul. 10, 2018

(86) PCT No.: PCT/US2018/041378
§ 371 (c)(1),
(2) Date: Jan. 2, 2020

(87) PCT Pub. No.: WO2019/018155
PCT Pub. Date: Jan. 24, 2019

(65) Prior Publication Data
US 2021/0137842 A1    May 13, 2021

Related U.S. Application Data

(60) Provisional application No. 62/538,936, filed on Jul. 31, 2017, provisional application No. 62/533,332, filed on Jul. 17, 2017.

(51) Int. Cl.
*A61K 9/20* (2006.01)
*A61K 9/24* (2006.01)
*A61K 9/00* (2006.01)
*A61K 31/155* (2006.01)
*A61K 31/40* (2006.01)
*A61K 31/41* (2006.01)

(52) U.S. Cl.
CPC ............ *A61K 9/209* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61K 31/155* (2013.01); *A61K 31/40* (2013.01); *A61K 31/41* (2013.01)

(58) Field of Classification Search
None
See application file for complete search history.

(56) References Cited

U.S. PATENT DOCUMENTS 8,574,625 B2 * 11/2013 Jain .................. A61K 31/55
424/465
2006/0204578 A1 * 9/2006 Vergez .............. A61K 31/4422
424/473

FOREIGN PATENT DOCUMENTS

| EP | 3 025 708 B1 | 8/2017 |
|----|--------------|--------|
| WO | 2008/95263 A1 | 8/2008 |
| WO | 2012/10977 A2 | 1/2012 |
| WO | 2015/066785 A1 | 5/2015 |

OTHER PUBLICATIONS

Nishanth et al., Research J. Pharma. Dosage Forms and Tech., p. 139-144, Jan. 1, 2013.
Ranpise, Nisharani et al., Indian Journal of Pharmaceutical Education and Research, vol. 48, No. suppl., Dec. 1, 2014.
Pan, Feng,et al., J. Gen. Intern. Med. 23(5): 611-14, 2008.
International Search Report of the International Searching Authority pertaining to International Application No. PCT/US2018/041378; dated Sep. 14, 2018; 6 pages.
Written Opinion of the International Searching Authority pertaining to International Application No. PCT/US2018/041378; dated Sep. 14, 2018; 9 pages.
Oh, J. H., Eun Lee, J., Jeong Kim, Y., Oh, T. O., Han, S., Jeon, E. K., . . . & Lee, Y. J. (2016). Designing of the fixed-dose gastroretentive bilayer tablet for sustained release of metformin and immediate release of atorvastatin. Drug development and industrial pharmacy, 42(2), 340-349.

* cited by examiner

*Primary Examiner* — Susan T Tran
(74) *Attorney, Agent, or Firm* — Macharri R. Vorndran-Jones

(57) ABSTRACT

The present invention relates to solid oral fixed dose compositions of metformin, atorvastatin, and valsartan, or their pharmaceutically acceptable salts, processes for the preparation thereof, and the use of the composition to treat certain diseases.

6 Claims, No Drawings

PHARMACEUTICAL COMPOSITIONS

The present invention relates to solid oral fixed dose compositions comprising metformin, atorvastatin, and valsartan; or the respective pharmaceutically acceptable salts, and processes for the preparation thereof. The solid oral compositions are useful in the treatment of a patient in need of treatment for Type 2 diabetes or pre-diabetes.

Type 2 diabetes is an increasingly prevalent disease that frequently leads to cardiovascular complications. Diabetes may be co-morbid with cardiovascular disease. The declining cardiovascular health of a patient with diabetes can be associated with increased medical expense and may result in death. There is desire for a single product oral treatment that can be used to treat or alleviate hyperglycemia associated with type 2 diabetes and alleviate or treat related co-morbidities such as hyperlipidemia and/or hypertension. The literature demonstrates that early intensive control of blood glucose, blood pressure, and blood cholesterol reduces the risks of major clinical outcomes, including death, in diabetes. See, Chan, J. C. N., *Lancet Diabetes Endocrinol.* 2014; 2: 969-79.

A three component tablet comprising metformin, atorvastatin, and valsartan is desired, however, the fixed dose combination presents several manufacturing and development challenges. There is a propensity for one or more of the components to react with each other during manufacturing, storage, distribution, and/or usage. In particular, the three component fixed dose tablet should be swallowed by the patient without crushing or splitting the tablet because premature contact between the components may result in undesirable impurities and undesirable physical form changes impacting drug product dissolution profiles. Pharmaceutical formulations containing two pharmaceutically active ingredients for use in treating Type 2 diabetes are known. Such formulations are commercially available. For example, Invokamet XR™ contains canagliflozin and metformin hydrochloride XR, Kombiglyze XR™ contains saxagliptin and metformin hydrochloride XR. There are additional known two component fixed dose compositions for use in treating Type 2 diabetes, each with metformin and either an SGLT2 inhibitor or a DPP4 inhibitor.

There continues to be a need for a single product to treat Type 2 diabetes by comprehensive management of blood sugar, lipid, and blood pressure. A fixed dose combination offers the advantages of convenience to patients and improved adherence for taking the medication at appropriate dose and intervals as prescribed (see, for example, *Pan et al., J. Gen. Intern. Med.* 23(5): 611-4, 2008). In particular, there is a need for a single combination product which is small enough that it can be swallowed easily by an adult, whilst being stable and whilst retaining the dissolution characteristics of the active components as found in the respective commercially available monotherapy products.

Compositions of this invention provide a treatment that may improve glycemic control in patients in need thereof, and further simultaneously treat hyperlipidemia and/or hypertension that may be related to or caused by increased blood glucose, in a patient in need thereof.

The present invention is a single product oral composition comprising the three fixed dose pharmaceutically active ingredients metformin, atorvastatin, and valsartan or pharmaceutically acceptable salts thereof, wherein the composition comprises a bilayer part comprising a metformin layer and valsartan layer; and an immediate release atorvastatin coating. The present invention provides fixed dose compositions which are stable and which have desirable dissolution characteristics.

In particular, the present invention is a solid oral fixed dose composition comprising
   a bilayer part comprising
   a. an extended release layer comprising metformin or a pharmaceutically acceptable salt thereof; and one or more excipients; and
   b. an immediate release layer comprising valsartan or a pharmaceutically acceptable salt thereof and one or more excipients;
   and further comprising an immediate release coating layer comprising atorvastatin, or a pharmaceutically acceptable salt thereof; and one or more excipients.

In an alternate embodiment, the present invention provides a solid oral fixed dose composition comprising:
   a. an extended release layer comprising metformin hydrochloride XR or metformin hydrochloride; and one or more excipients;
   b. an immediate release layer comprising valsartan and one or more excipients;
   c. an immediate release coating layer comprising atorvastatin, or a pharmaceutically acceptable salt thereof; and one or more excipients.

In one embodiment, the metformin or pharmaceutically acceptable salt thereof is metformin hydrochloride.

In one embodiment, the extended release layer comprises metformin hydrochloride, hypromellose and microcrystalline cellulose. Preferably, the extended release layer further comprises magnesium stearate and colloidal silicon dioxide.

In one embodiment, the metformin hydrochloride is present in the form of granules which additionally comprise povidone and magnesium stearate. In a further embodiment, the metformin containing extended release layer additionally comprises sodium stearyl fumarate or magnesium stearate; microcrystalline cellulose; and colloidal silicon dioxide.

In one embodiment, the metformin hydrochloride is present in a unit dose strength selected from the group consisting of about 250, about 500 and about 750 mg, preferably about 500 mg.

In one embodiment, valsartan or pharmaceutically acceptable salt thereof is valsartan.

In one embodiment, the valsartan is present in a unit dose strength selected from the group consisting of about 40, about 50, about 60, about 70 and about 80 mg preferably about 80 mg.

In one embodiment, atorvastatin or pharmaceutically acceptable salt thereof is atorvastatin calcium trihydrate.

In one embodiment, the atorvastatin calcium trihydrate is present in a unit dose strength selected from the group consisting of about 5, about 10, about 15 and about 20 mg, preferably about 10 mg.

An embodiment of this invention is a solid oral fixed dose composition comprising
   a bilayer part comprising
   a) an extended release layer comprising metformin or a pharmaceutically acceptable salt thereof wherein the metformin unit dose strength is about 500 mg;
   b) an immediate release layer comprising valsartan or a pharmaceutically acceptable salt thereof, wherein the valsartan unit dose strength is about 80 mg;
   and further comprising
   an immediate release coating layer comprising atorvastatin, or a pharmaceutically acceptable salt thereof, wherein the atorvastatin unit dose strength is about 10 mg.

In a further embodiment, the solid oral fixed dose composition comprises
  a bilayer part comprising:
  a. an extended release layer comprising metformin hydrochloride in a unit dose strength of about 500 mg;
  b. an immediate release layer comprising valsartan in a unit dose strength of about 80 mg;
  and further comprising
  an immediate release coating layer comprising atorvastatin calcium trihydrate in a unit dose strength of about 10 mg.

In an alternate embodiment, the present invention provides, a solid oral fixed dose composition comprising
  a. an extended release layer comprising metformin hydrochloride or metformin XR; and one or more excipients;
  b. an immediate release layer comprising valsartan and one or more excipients;
  c. an immediate release coating layer comprising atorvastatin calcium trihydrate; and one or more excipients.

In one embodiment, the composition is a tablet, preferably a tablet that is of pharmaceutically acceptable size to be swallowed intact by an adult.

The present invention provides a process for preparing a solid fixed dose composition of the invention comprising forming a compressed bilayer part comprising:
  a. an extended release layer comprising metformin, or a pharmaceutically acceptable salt thereof, and one or more excipients; and
  b. an immediate release layer comprising valsartan, or a pharmaceutically acceptable salt thereof, and one or more excipients;
  and coating with an immediate release coating layer comprising atorvastatin, or a pharmaceutically acceptable salt thereof, and one or more excipients.

Also provided herein is a process for preparing a solid oral fixed dose composition comprising
  a. an extended release layer comprising metformin hydrochloride and one or more excipients
  b. an immediate release layer comprising valsartan or a pharmaceutically acceptable salt thereof and one or more excipients
  c. an immediate release coating layer comprising atorvastatin or a pharmaceutically acceptable salt thereof and one or more excipients,
  wherein the fixed dose composition is prepared as a compressed bilayer tablet comprising layers a) metformin, and layer b) valsartan; and coated with an active coating layer c) atorvastatin.

In one embodiment, the pH of the immediate release coating layer comprising atorvastatin, or a pharmaceutically acceptable salt thereof, is maintained at or above pH 6.

In an embodiment, the fixed dose composition further comprises an intermediate coat layer between the bilayer part, which comprises the metformin and valsartan layers, and the immediate release coating layer containing the atorvastatin. An immediate release top coat may also be applied on top of the immediate release coating layer comprising atorvastatin, or a pharmaceutically acceptable salt thereof.

The fixed dose composition is advantageously useful for the treatment of a patient in need of treatment for Type 2 diabetes or a patient at risk for developing Type 2 diabetes. The fixed dose composition may be useful for treating a patient in need of treatment for pre-diabetes. The fixed dose composition is useful in the treatment of a patient in need of treatment for metabolic syndrome. The fixed dose composition can be useful for treating a patient in need of treatment for pre-diabetes and one or two conditions selected from the group consisting of hypertension and hyperlipidemia. The fixed dose composition can be useful for treating a patient in need of treatment for Type 2 diabetes and one or two conditions selected from the group consisting of hypertension and hyperlipidemia.

The present invention provides a method of treating Type 2 diabetes mellitus in a patient in need thereof comprising administering an effective amount of a composition of the invention. The present invention further provides a method of treating pre-diabetes in a patient in need thereof comprising administering an effective amount of a composition of the invention. The present invention further provides a method of treating metabolic syndrome in a patient in need thereof comprising administering an effective amount of a composition of the invention.

The present invention provides a composition of the invention for use in therapy. The present invention further provides a composition of the invention for use in the treatment of Type 2 diabetes mellitus. The present invention further provides a composition of the invention for use in the treatment of pre-diabetes. The present invention further provides a composition for use in the treatment of metabolic syndrome.

The present invention provides the use of a composition of the invention in the manufacture of a medicament for the treatment of Type 2 diabetes mellitus. The present invention further provides the use of a composition of the invention in the manufacture of a medicament for the treatment of pre-diabetes. The present invention further provides the use of a composition of the invention in the manufacture of a medicament for the treatment of metabolic syndrome.

In a particular embodiment, the patient being treated for Type 2 diabetes or pre-diabetes is also in need of treatment for hypertension and/or hyperlipidemia.

In a particular embodiment, the fixed dose composition of the invention is administered to the patient once per day.

Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S.M. Berge, et al., "Pharmaceutical Salts," *Journal of Pharmaceutical Sciences*, Vol. 66, No. 1, January 1977.

In a preferred embodiment, the pharmacokinetic parameters of area under the curve (AUC) and maximum concentration ($C_{max}$) for each component are within a 90% confidence interval of 80-125% of the regulatory approved monotherapy.

As used herein, "about" means plus or minus 10%. Preferably, the term "about" means plus or minus 5%.

The term "tablet" as used herein means an oral pharmaceutical dosage formulation of all sizes and shapes. In an embodiment, the tablet is compressed. In an embodiment, the tablet may be swallowed by an adult without breaking or crushing the tablet.

The term "pre-diabetes" is a condition wherein the individual is pre-disposed to the development of Type 2 diabetes mellitus.

The term "treating" or "treatment" comprise therapeutic treatment of a patient diagnosed with a condition. Therapeutic treatment may be symptomatic treatment in order to relieve the symptoms of a condition or may stop or slow the progression of the condition.

As used herein "pharmaceutically acceptable size" means a size that is generally suitable for swallowing by an adult intact without fracture, breaking, or crushing. Generally, the largest dimension of the tablet should not exceed about 22 mm. As used herein, the largest cross sectional area means the largest cross sectional area of the tablet that lies in a plane perpendicular to the longest axis of the tablet. If the shape is non-conventional, such as a pentagon, triangle, diamond, and the like, then the largest cross sectional area will be the area of the smallest circle, oval, or ellipse that would completely enclose the cross sectional shape. In an embodiment, the fixed dose composition is oval in shape with dimensions of less than 22 mm by 11 mm, preferably less than 20 mm by 11 mm. It may be preferred that the pharmaceutically acceptable size is an oval or oblong shape of less than or equal to about 20 mm by 10 mm, preferably about 14 mm by 9 mm. It may be preferred that the pharmaceutically acceptable size is a round shape less than about 11 mm diameter. The thickness of the fixed dose composition may vary but preferably it is in the range of 7 mm to 9 mm.

As used herein, the term "extended release" means that the active is gradually released from the composition. Generally, the active is released over a period of up to 12 hours from administration. Preferably, the active, in particular metformin or a pharmaceutically acceptable salt thereof, is released over a period of between 10 and 12 hours. The release of the active from the composition (the dissolution) is measured in pH 6.8 buffer using conventional dissolution testing.

As used herein, the term "immediate release" means that the majority of the active is released quickly from the composition. Preferably, at least 80% of the active is released within 30 minutes from administration, preferably within 15 minutes. The release of the active from the composition (the dissolution) is measured in pH 6.8 buffer using conventional dissolution testing.

As used herein, the term "hypromellose" means hydroxypropyl methylcellulose (HPMC). An example of a commercially available hypromellose is Methocel™ K100M.

The term "metformin" as used herein refers to metformin or a pharmaceutically acceptable salt thereof. Metformin is a well-known, commercially available pharmaceutical for use in treating type 2 diabetes. Metformin is chemically described as 1,1-dimethylbiguanide. Such pharmaceutically acceptable salts of metformin include for example, metformin hydrochloride, metformin fumarate salt, metformin succinate salt, metformin hydrobromide salt, metformin p-chlorophenoxy acetate salt, and metformin embonate, and other known metformin salts of mono and dibasic carboxylic acids. A metformin hydrochloride salt is a preferred pharmaceutically acceptable salt.

Metformin is preferably administered as an extended release formulation, also known as XR or ER, of metformin hydrochloride. Exemplary metformin extended release formulations are known, for example, U.S. Pat. Nos. 6,723,340, 6,340,475, and 6,660,300.

It is preferred that the metformin or pharmaceutically acceptable salt thereof is present in an extended release formulation comprising a diffusion rate controlling polymer such as, but not limited to, hypromellose, diluents such as microcrystalline cellulose, magnesium stearate, and colloidal silicon dioxide. A further preferred metformin layer comprises a granulation of metformin hydrochloride with povidone, and magnesium stearate, wherein the metformin granulation is mixed with hypromellose, and microcrystalline cellulose, silicon dioxide, and magnesium sterate. A further preferred metformin layer comprises a granulation of metformin hydrochloride about 95% by weight, povidone about 4.5% by weight, and magnesium stearate about 0.5% by weight. In a further embodiment, the metformin granulation is combined with hypromellose, microcrystalline cellulose, magnesium stearate, and colloidal silicon dioxide.

In an embodiment, the metformin, or pharmaceutically acceptable salt thereof, is present in the form of granules. In a further embodiment, the metformin granules additionally comprise a binder, for example povidone and sodium carboxymethylcellulose, and optionally, a lubricant, for example magnesium stearate, sodium stearyl fumarate and stearic acid. The preferred binder in the granules is povidone. Povidone may be present in an amount of up to 5% by weight of the granules, preferably about 4.5%. The preferred lubricant in the granules is magnesium stearate. Magnesium stearate may be present in an amount of up to 1% by weight of the granules, preferably about 0.5%.

The preferred dissolution control polymer in the extended release layer comprising metformin or a pharmaceutically acceptable salt thereof is hypromellose. Hypromellose K200M, Hypromellose K100M and Hypromellose K15M are preferred. Hypromellose K100M is particularly preferred. Hypromellose may be present in an amount of 20 to 45% by weight of this extended release layer, preferably 33 to 42% by weight and more preferably 35 to 39% by weight.

Preferably, the hypromellose has a viscosity from about 4,000 mPa·s to about 200,000 mPa·s, more preferably from about 50,000 to about 200,000 mPa·s, and more preferably 80,000 mPa·s to 120,000 mPa·s, measured as a 2% solution in water. A viscosity of about 100,000 mPa·s (K100M) may be preferred.

In an embodiment, the extended release layer comprising metformin, or a pharmaceutically acceptable salt thereof, comprises, in addition to the metformin granules, microcrystalline cellulose. Microcrystalline cellulose may be present in an amount of 0.5 to 15% by weight of this extended release layer, more preferably 5 to 10% by weight.

In a further embodiment, the extended release layer comprising metformin, or a pharmaceutically acceptable salt thereof, comprises, in addition to the metformin granules, colloidal silicon dioxide. Colloidal silicon dioxide may be present in an amount of up to 1% by weight of this extended release layer.

In a further embodiment, the extended release layer comprising metformin, or a pharmaceutically acceptable salt thereof, comprises in addition to the metformin granules, a lubricant, for example sodium stearyl fumarate, magnesium stearate or stearic acid. The preferred lubricant is sodium stearyl fumarate. The lubricant, in particular sodium stearyl fumarate, may be present in an amount of up to 1% by weight of this extended release layer.

The extended release layer of the composition which comprises metformin or a pharmaceutically acceptable salt thereof can be prepared using common tableting methods that involve mixing, comminution, and fabrication steps commonly practiced and well known to those skilled in the art. It may be preferred that the metformin is dry mixed.

The extended release layer comprising metformin, or a pharmaceutically acceptable salt thereof, preferably has a total weight of no more than 1000 mg. More preferably, it has a total weight of 900 mg to 1000 mg. In a particular embodiment, this layer has a total weight which is less than the total tablet weight of the regulatory approved monotherapy product Glucophage® XR (about 1025 mg).

Valsartan is a well-known commercially available pharmaceutical for use in treating hypertension. Valsartan is chemically described as N-(1-oxopentyl)-N-[[2'-(1H-tetrazol-5-yl)[1,1-biphenyl]-4-yl]methyl]-L-valine. Valsartan is a free acid with pKas of 3.9 and 4.7. The most common solid form of commercially available valsartan is the semi-crystalline form, also sometimes called crystalline mesophase possessing a melting endotherm, $T_m$ of about 100° C.

In an embodiment, the immediate release layer comprising valsartan, or a pharmaceutically acceptable salt thereof, comprises microcrystalline cellulose. Microcrystalline cellulose may be present in an amount of 40 to 60% by weight of this immediate release layer. Alternatively, other common diluents and fillers such as lactose or mannitol may be added.

In a further embodiment, the immediate release layer comprising valsartan, or a pharmaceutically acceptable salt thereof, comprises colloidal silicon dioxide. Collodial silicon dioxide may be present in an amount of 0.5 to 3% by weight of this immediate release coating layer.

In a further embodiment, the immediate release layer comprising valsartan, or a pharmaceutically acceptable salt thereof, comprises a lubricant, for example sodium stearyl fumarate, magnesium stearate or stearic acid. The preferred lubricant is sodium stearyl fumarate. The lubricant, in particular sodium stearyl fumarate, may be present in an amount of 0.5 to 3% by weight of this immediate release layer.

In a further embodiment, the immediate release layer comprising valsartan, or a pharmaceutically acceptable salt thereof, comprises a disintegrant, for example croscarmellose sodium or crospovidone. The preferred disintegrant is croscarmellose sodium. The disintegrant, in particular croscarmellose sodium, may be present in an amount of 2 to 15% by weight of this immediate release layer.

In a further embodiment, the immediate release layer comprising valsartan, or a pharmaceutically acceptable salt thereof, comprises iron oxide red.

Atorvastatin is a well-known commercially available pharmaceutical for use in treating hyperlipidemia. Atorvastatin calcium trihydrate ([R—(R*,R*)]-2-(4-fluorophenyl)-β, δ-dihydroxy-5-(1-methylethyl)-3-phenyl-4-[(phenylamino)carbonyl]-1H-pyrrole-1-heptanoic acid, calcium salt (2:1) trihydrate) is the most common solid form of commercial atorvastatin drug substance and possesses known pH dependent chemical instability. At pH<6, atorvastatin degrades to an undesired byproduct, a lactone. The acid-sensitivity of atorvastatin raises a potential problem when formulating with the active valsartan, a free acid. Many common tableting excipients have a surface pH<6, that can lead to atorvastatin lactone formation when mixed and during storage. Thus, a straightforward combination of atorvastatin with many common tableting excipients produces an unstable product under typical ICH storage conditions. Atorvastatin is therefore often wet granulated with a basic agent, e.g. calcium carbonate, to raise the local pH to prevent lactone formation.

Atorvastatin is often granulated with basic excipients, such as the alkaline metal salts calcium carbonate or sodium bicarbonate, to decrease lactone formation. Valsartan, a free acid, has been shown to form salts with such alkaline metals salts. It is challenging to formulate valsartan in the fixed dose composition in the presence of stabilizing alkaline metal salt excipients to avoid physical conversion of the valsartan to a salt form that may have different dissolution properties thereby impacting in-vivo dissolution and absorption.

In an embodiment, the immediate release coating layer comprising atorvastatin, or a pharmaceutically acceptable salt thereof, comprises a film former, for example, hypromellose or polyvinyl acetate. The preferred film former is hypromellose. The film former, in particular hypromellose, may be present in an amount of 40 to 90% by weight of this immediate release coating layer.

In a further embodiment, the immediate release coating layer comprising atorvastatin, or a pharmaceutically acceptable salt thereof, comprises a plasticizer, for example PEG400, PEG3350, PEG8000 or triacetin. PEG3350, PEG8000 and triacetin are preferred. Triacetin is particularly preferred. The plasticizer, in particular triacetin, may be present in an amount of 3 to 10% by weight of this immediate release coating layer.

In a further embodiment, the immediate release coating layer comprising atorvastatin, or a pharmaceutically acceptable salt thereof, comprises an anti-tacking agent, for example talc.

In a further embodiment, the immediate release coating layer comprising atorvastatin, or a pharmaceutically acceptable salt thereof, comprises calcium carbonate. Calcium carbonate may be present in an amount of 5 to 20% by weight of this immediate release coating layer.

Other common coating components for example opacifiers (such as titanium dioxide) and pigments may be included in the immediate release coating layer.

The unit dose strength of metformin, or pharmaceutically acceptable salt thereof, in particular metformin hydrochloride, for incorporation into the fixed-dose composition is preferably about 250 to about 1000 mg. A preferred unit dose strength of metformin, or pharmaceutically acceptable salt thereof, in particular metformin hydrochloride, is about 250, about 500, about 750, about 850, or about 1000 mg. A further preferred unit dose strength of metformin, or pharmaceutically acceptable salt thereof, in particular metformin hydrochloride, is selected from the group consisting of about 250, about 500 and about 750 mg. A preferred unit dose strength of metformin, or a pharmaceutically acceptable salt thereof, in particular metformin hydrochloride, in the fixed dose composition is about 500 mg.

The unit dose of atorvastatin or pharmaceutically acceptable salt thereof, in particular atorvastatin calcium trihydrate, for incorporation into the fixed dose composition is preferably 5 to 20 mg. A preferred unit dose strength of atorvatstatin or pharmaceutically acceptable salt thereof, in particular atorvarstatin calcium trihydrate, is about 5, about 10, about 15, or about 20 mg. A preferred unit dose strength of atorvastatin or pharmaceutically acceptable salt thereof, in particular atorvarstatin calcium trihydrate, is about 10 mg.

The unit dose of valsartan or pharmaceutically acceptable salt thereof, in particular valsartan, for incorporation into the fixed dose composition is preferably 40 to 80 mg. A preferred unit dose strength of valsartan or pharmaceutically acceptable salt thereof, in particular valsartan, is about 40, about 50, about 60, about 70, or about 80 mg. A further preferred unit dose strength of valsartan, or a pharmaceutically acceptable salt thereof, in particular valsartan, is about 80 mg.

Tablets may be prepared by direct compression or other commonly used processes such as wet granulation of dry granulation (roller compaction). The addition of lubricants may be helpful and are known in the art. Typical lubricants are for example, magnesium stearate, stearic acid, and hydrogenated vegetable oil.

Additional excipients may be added, provided that the overall size of the tablet is minimized. For example, granulating aids, binders, and additives to enhance powder flowability, tablet hardness, and tablet friability.

As used herein "coating" and "coat" means a layer added to the bilayer part of the composition. The skilled artisan will recognize that a coating may be added to enhance the pharmaceutical elegance, taste mask, enhance stability, coloring, ease of swallowing, and the like.

As used herein "active coating" or "active coat" means a coating layer containing a pharmaceutically active ingredient, such as atorvastatin. The pharmaceutically active ingredient, atorvastatin, is used in the coating suspension or solution to form an "active coating" layer over the bilayer part of the composition.

As used herein "clear coating" means a tablet coating that does not change the color of the original tablet and does not contain an active pharmaceutical agent. Clear coating is optionally added over the active coating.

A layer may be provided between pharmaceutically active layers or as a coat to enhance stability, pharmaceutical elegance, and/or lamination of the active layer(s).

As used herein "intermediate coat" means a layer which is between the bilayer part and the active coating.

As used herein "top coat" means the outer most layer of the composition. The top coat can be colored, opaque or clear.

As used herein "PVA" means polyvinyl acetate.

The skilled person will readily appreciate that the fixed dose compositions of the present invention may be prepared using various techniques known in the art. This section provides examples of techniques and conditions which may be used but is in no way limiting.

Valsartan is mixed with a cellulosic excipient and other appropriate tableting excipients. This layer is compressed (as layer 2) onto a hypromellose matrix tablet of metformin (layer 1), to form a bilayer tablet. The extended release layer comprising metformin or a pharmaceutically acceptable salt thereof is reduced to the smallest feasible size of 700 to not more than 1000 mg, preferably 800 to 1000 mg, more preferably 900 mg to 1000 mg, that maintains a dissolution profile similar to that of the regulatory agency approved mono product (Glucophage® XR). Atorvastatin is then applied as a component of an immediate release film onto the bilayer tablet. An intermediate coat and/or top coat may optionally be applied to the tablet to further improve stability and/or elegance. The selection of an immediate release film coating system that provides a stable environment, specifically, an appropriate pH, is required to ensure the atorvastatin remains stable. Common film coating systems include HPMC and PVA based systems. HPMC based film coating may be a preferred embodiment. Addition of pH modifying agents, such as calcium carbonate, may be incorporated into the coating system to achieve the desired pH and maintain active ingredient stability.

1) Valsartan and appropriate tableting excipients are blended together using suitable pharmaceutical blending equipment. The valsartan blend may be granulated using suitable granulation equipment to improve flow. Extra-granular excipients may also be added per conventional granulation practice.
2) Metformin, hypromellose, and other appropriate tableting excipients are blended together using suitable pharmaceutical blending equipment. Metformin may be granulated or milled using conventional processes to improve process.
3) The final valsartan blend and the final metformin blend are combined at the desired ratios to produce a bilayer tablet using suitable pharmaceutical bilayer tablet compression equipment.
4) The bilayer core tablets may or may not be sub-coated (intermediate coat).
5) The atorvastatin drug substance is dispersed in an aqueous film coating system with pH neutral excipients and optionally a basic excipient. In an embodiment the film coat may preferably comprise a film former, a plasticizer, and optionally an anti-tacking agent and pH modifier. In an embodiment, the film coat may preferably comprise a film former and an anti-tacking agent. A preferred film former is selected from hypromellose and polyvinyl acetate. A preferred plasticizer is selected from the group consisting of PEG 3350, PEG 8000, and triacetin. One preferred anti-tacking agent is talc. The film coat may further comprise one or more pH modifying agents such as calcium carbonate, to make a coating suspension.
6) The bilayer core tablets are then coated with the atorvastatin suspension or solution to the desired weight gain to achieve the target dose.
7) A top coat may or may not be applied to the tablets.

The fixed dose composition may also contain one or more additional formulation ingredients selected from a wide variety of excipients known in the pharmaceutical arts. Such ingredients may include, but are not limited to, diluents, compression aids, binders, glidants, disintegrants, lubricants, colors, flavors, flavor enhancers, sweeteners and preservatives.

It is preferred that the fixed dose composition may be swallowed by an adult without crushing or breaking. The oral composition may be administered once per day or twice per day, as determined by a physician. It is especially preferred that the oral composition may be administered once per day.

Appropriate process and packaging controls to ensure control of water activity to levels may be beneficial in preparation of a pharmaceutically acceptable stable product.

Specific tablet shape (e.g. modified oval or capsule shape), and design, (e.g. two color tablet) may be incorporated to reduce visual bulkiness, facilitate swallowing, and maintain tablet strengths.

EXAMPLE 1

A Fixed Dose Combination Tablet Comprising 500 mg Metformin HCl, 80 mg Valsartan, 10 mg Atorvastatin Calcium Trihydrate The composition is prepared using the components set forth in Table A, below. Hypromellose, colloidal silicon dioxide, metformin HCl granules (95% granulation potency), and microcrystalline cellulose are pre-blended in a bag for 1 to 2 minutes, de-lumped and blended again in a V-blender for 10 minutes. After sieving, magnesium stearate is charged to the same V-blender and the mixture is blended for 3 minutes.

For layer 2, valsartan, microcrystalline cellulose, colloidal silicon dioxide, iron oxide red, and croscarmellose sodium are pre-blended in a bag for 1-2 minutes, de-lumped, and blended in a V-blender for 10 minutes. After sieving, the magnesium stearate is charged to the same V-blender and the mixture is blended for 3 minutes.

The blends are loaded into separate hoppers in a bilayer tablet press. Using modified oval tooling (0.3605×0.7435 inch), bilayer tablets are prepared targeting a 900 mg metformin layer weight and a 170 mg valsartan layer weight.

The coating suspensions are prepared using commercially available coating system (for example, Opadry, 03K19229 Clear from Colorcon, West Point, Pa., USA). The intermediate coat and top coat suspension are prepared by dispersing/dissolving the coating system in deionized water to 5% total solids content and mixing for not less than 30 minutes. The suspension is prepared to a batch size of 1.28 kg, which includes an excess. The pH of the coating suspension is measured as 6.44.

The active coat is prepared in a substantially the same as the intermediate coat and top coat; however, the total solids content is comprised of 1.08% atorvastatin calcium trihydrate and 3.92% coating system giving a total solids content of 5%. The coating system is first dispersed/dissolved in deionized water and mixed for not less than 30 minutes. The atorvastatin calcium trihydrate is added to the coating mixture and mixed for not less than 30 minutes to fully disperse the atorvastatin. The pH of the coating suspension is measured as 6.69.

Core bilayer tablets are loaded into a pan coater with an 11 inch coating pan and a Spraying System Spray Nozzle Setup. Tablets are pre-warmed to 40° C. in the pan coater. The average weight of 30 pre-warmed tablets is measured. For the optional intermediate coat application, the tablets are coated to a theoretical weight gain of 1%, assuming a core tablet weight of 1070 mg. The coating conditions, spray rate, inlet temperature, and flow volume, are adjusted to maintain a temperature of 40° C. during coating. Once the intermediate coat weight gain is achieved, the active coat is then applied in a substantially the same manner, targeting a theoretical weight gain of 4.6729%, assuming a core tablet weight of 1070 mg. The coating conditions are adjusted to maintain a temperature of 40° C. during coating. Once the active-coat weight gain is achieved, the optional top coat is applied in substantially the same way as the intermediate coat, targeting a theoretical weight gain of 1%, assuming a core tablet weight of 1070 mg. The coating conditions are adjusted to maintain a temperature of 40° C. during coating. Tablets are then dried in the pan coater for 4-6 minutes at 60° C. and then discharged into a bag.

TABLE A

| Component | Amount (mg) |
|---|---|
| Metformin-Layer-1 | |
| Metformin HCl granules | 526.32 |
| Metformin HCl | 500 |
| Povidone | 23.68 |
| Magnesium stearate | 2.64 |
| Hypromellose 2208, 100,000 mPa.s viscosity | 315.00 |
| Microcrystalline cellulose, silicified | 45.18 |
| Magnesium stearate | 9.00 |
| Colloidal silicon dioxide | 4.5 |
| Total layer 1 | 900 |
| Valsartan-Layer-2 | |
| Valsartan | 80.00 |
| Microcrystalline cellulose, silicified | 78.66 |
| Croscarmellose sodium | 7.00 |
| Iron oxide red | 0.14 |
| Magnesium stearate | 2.5 |
| Colloidal silicon dioxide | 1.70 |
| Total layer 2 | 170 |
| Intermediate coat | |
| Hypromellose 2910, 6,000 mPa.s viscosity | 9.00 |
| Triacetin | 0.90 |
| Talc | 0.80 |
| Total intermediate coat | 10.70 |
| Active coat | |
| Atorvastatin calcium | 10.85 |
| Hypromellose 2910, 6,000 mPa.s viscosity | 32.92 |
| Triacetin | 3.29 |
| Talc | 2.94 |
| Total active coat | 50.00 |
| Top coat | |
| Hypromellose 2910, 6,000 mPa.s viscosity | 9.00 |
| Triacetin | 0.90 |
| Talc | 0.80 |
| Total top coat | 10.70 |
| Total coated tablet weight | 1141.4 |

The final fixed dose combination tablet is oval in shape and measures 9.2 mm×18.9 mm.

The tablet size and weight are acceptable to the patient for oral consumption without fracturing the tablet. The formulation comprising fixed dose combination of Example 1 is consistent with pharmaceutically elegant formulations that may be swallowed without fracture of the tablet.

EXAMPLE 2

The fixed dose composition is prepared substantially as described for Example 1, except that PEG400 is used instead of triacetin at each occurrence.

Alternate Preparation 1

Wet Granulation

For comparison, a bilayer tablet is prepared using a wet granulation formulation.
1) Atorvastatin calcium trihydrate is wet granulated with calcium carbonate and the granulating excipients: hydroxypropyl cellulose, polysorbate 80, microcrystalline cellulose, lactose, and croscarmellose sodium, using water as the granulating liquid.
2) The resulting wet granules are thoroughly dried and sized using appropriate pharmaceutical equipment.
3) Valsartan and the appropriate tableting excipients are pre-blended together using suitable pharmaceutical blending equipment.
4) The dried and sized atorvastatin granules are then combined with the valsartan pre-blend and blended together using suitable pharmaceutical blending equipment. This blend is then lubricated with an appropriate excipient using suitable pharmaceutical blending equipment.
5) Metformin, hypromellose and other appropriate tableting excipients are blended together using suitable pharmaceutical blending equipment.
6) The two blends are then combined at the desired ratios, using suitable pharmaceutical tablet compression equipment, to produce a bilayer tablet of equivalent dose as the fixed dose combination of Example 1.

Alternate Preparation 2

Dry Mix

A bilayer tablet is prepared using a simple dry mix.
a. Atorvastatin calcium trihydrate is pre-blended (dry) with a stabilizing excipient, calcium carbonate, using suitable pharmaceutical blending equipment.
b. The atorvastatin pre-blend, valsartan, and appropriate tableting excipients are blended together using suitable pharmaceutical blending equipment. This blend is lubricated with an appropriate excipient using suitable pharmaceutical blending equipment
c. Metformin hydrochloride, hypromellose, and other appropriate tableting excipients are blended together using suitable pharmaceutical blending equipment.
d. The two blends are then combined at the desired ratios, using suitable pharmaceutical tablet compression equipment, to produce a bilayer tablet of equivalent dose as the composition of Example 1.

Tablets are placed on an accelerated stability study and the primary degradant, the atorvastatin lactone, is monitored to gauge the effectiveness of the stabilization of atorvastatin in the dosage form. Samples are stored in an open dish at elevated controlled temperature and humidity. Samples are tested for the atorvastatin lactone impurity using HPLC with UV detection. The data provided in Table B and Table C, demonstrate the stability of the Example 1 and Example 2 compositions. The data provided in Table D and Table E suggest that the compositions of Example 1 and Example 2 provide dissolution profiles that are comparable to the respective regulatory agency approved mono-product.

Atorvastatin Stability

Unexpectedly, the composition of Example 2 resulted in more atorvastatin lactone formation than expected.

TABLE B

| Presentation | % atorvastatin lactone measured on stability: 40° C./50% RH | | | |
|---|---|---|---|---|
| | Initial | 1 week | 2 weeks | 4 weeks |
| Alternate Preparation 2 | 0.36 | 0.40 | 0.45 | 0.44 |
| Alternate Preparation 1 | 0.38 | 0.62 | 0.79 | 0.93 |
| Example 2 | 0.46 | 0.76 | 0.99 | 1.25 |

Also surprisingly, the pH of the coating suspension of atorvastatin in Example 2 is measured as a pH=4.53 despite all excipients in the coating having no acidic functionality, and being neutral in nature.

The composition of Example 1 is compared to the Alternate Preparation 2 in an open dish stressed stability study. Example 1 is found to have superior stability, with no measureable increase of the lactone impurity found in Example 1. This demonstrates that separating the atorvastatin from the valsartan and adding it to a coating layer has a favourable effect on stability.

TABLE C

| Presentation | % atorvastatin lactone measured on stability: | | | | |
|---|---|---|---|---|---|
| | | 50° C./ 55% RH | | 55° C./ 45% RH | |
| | Initial | 1 day | 2 day | 1 day | 2 day |
| Example 1 | 0.28 | 0.26 | 0.27 | 0.26 | 0.26 |
| Alternate Preparation 2 | 0.28 | 0.62 | 0.99 | 0.62 | 0.90 |

Dissolution

Dissolution of the two immediate release actives are measured using a USP apparatus II and HPLC with UV detection and 50 mM pH 6.8 phosphate buffer at 37° C. as the media. The film coated prototypes compare favorably to the regulatory approved mono products in dissolution testing. The regulatory approved atorvastatin product is Lipitor® and the regulatory approved valsartan product is Diovan®.

TABLE D

| Presentation | Average (n = 6) % release at 30 minutes | |
|---|---|---|
| | Atorvastatin | Valsartan |
| Regulatory approved mono product | 98 | 100 |
| Example 1 | 90 | 104 |
| Example 2 | 92 | 104 |

Dissolution of metformin is measured in 50 mM pH 6.8 phosphate buffer at 37° C. using a USP apparatus II with HPLC and UV detection. The percent release of metformin in the film coated prototypes compare favorably to the regulatory approved mono product (Glucophage® XR) over 10 hours.

TABLE E

| Time (hr) | Average (n = 6) % release metformin HCl | |
|---|---|---|
| | Example 2 | Regulatory approved mono product |
| 1 | 24 | 26 |
| 3 | 47 | 48 |
| 6 | 70 | 68 |
| 10 | 90 | 85 |
| | Example 1 | |
| 1 | 24 | 26 |
| 3 | 48 | 48 |
| 6 | 73 | 68 |
| 10 | 91 | 85 |

Size of Metformin Layer and Dissolution Rate

The dissolution rate of metformin hydrochloride in two metformin-valsartan bilayer tablets in which the total weight of metformin layer was reduced relative to the commercially available metformin product Glucophage® XR was measured and compared to the dissolution rate in Glucophage® XR.

The bilayer tablets are prepared substantially as described in Example 1. The composition of the bilayer tablet is set out below in Table F.

TABLE F

| Component | Amount mg | % wt of layer |
|---|---|---|
| Metformin HCl granules (95%)* | 526 | 56.9 |
| HPMC | 343 | 37.1 |
| Microcrystalline Cellulose | 47 | 5.1 |
| Sodium stearyl fumarate | 9 | 1.0 |
| TOTAL layer | 925 | 100.0 |
| Valsartan | 80 | 38.1 |
| Microcrystalline cellulose | 92 | 43.8 |
| Croscarmellose sodium | 31.5 | 15.0 |
| Silicon dioxide | 2.1 | 1.0 |
| Iron oxide red | 0.2 | 0.1 |
| Sodium stearyl fumarate | 4.2 | 2.0 |
| TOTAL layer | 210 | 100.0 |
| Metformin HCl granules (95%)* | 526 | 53.9 |
| HPMC | 363.2 | 37.2 |
| Microcrystalline cellulose | 76.1 | 7.8 |
| Sodium stearyl fumarate | 9.8 | 1.0 |
| TOTAL layer | 975.1 | 100.0 |
| Valsartan | 80 | 27.2 |
| Microcrystalline cellulose | 154.9 | 52.7 |
| Croscarmellose sodium | 44.1 | 15.0 |
| Silicon dioxide | 7.4 | 7.5 |
| Iron oxide red | 0.3 | 0.1 |
| Sodium stearyl fumarate | 7.4 | 2.5 |
| TOTAL layer | 294.1 | 100.0 |

*Granules composed of: 95% wt metformin HCl, 0.5% wt magnesium stearate and 4.5% wt povidone.

Dissolution of metformin hydrochloride is measured in 50 mM pH 6.8 phosphate buffer at 37° C. using a USP apparatus I. The results are set out below in Table G.

TABLE G

| | % metformin HCl released | | | | | |
|---|---|---|---|---|---|---|
| | 60 min | 120 min | 180 min | 360 min | 600 min | 720 min |
| Glucophage ® XR 1025 mg tablet | 31.2 | 45.4 | 56.1 | 77.6 | 95.5 | 100 |
| Bilayer tablet with 925 mg metformin layer total wt | 31.9 | 46.8 | 58.7 | 80.3 | 96.7 | 100 |
| Bilayer tablet with 975 mg metformin layer total wt | 30.2 | 45.3 | 56.7 | 78.6 | 96.3 | 100 |

It is well known that the surface area to volume ratio (SA/Vol) of a matrix XR tablet impacts the release rate of the drug, with a higher SA/Vol resulting in a faster release. As the Glucophage® XR tablet is oval (unit dose of metformin HCl is 500 mg) in shape and weighs about 1025 mg, it would be expected that a tablet of similar composition and shape, only smaller in mass, should have a faster dissolution rate. However, these data surprisingly show that the size of the metformin layer can be reduced without resulting in a measurable difference in dissolution rate.

We claim:

1. A solid oral fixed dose composition comprising a bilayer tablet comprising
    a. an extended release layer comprising metformin hydrochloride in a unit dose strength of about 500 mg, and one or more excipients; and
    b. an immediate release layer comprising valsartan in a unit dose strength of about 80 mg, and one or more excipients;
    and further comprising an immediate release coating layer comprising atorvastatin calcium trihydrate in a unit dose strength of about 10 mg, and one or more excipients, wherein the immediate release coating layer is coated over the bilayer tablet.

2. The composition according to claim 1 wherein the tablet is of a pharmaceutically acceptable size to be swallowed intact by an adult.

3. The composition according to claim 1 wherein the metformin hydrochloride is present in the form of granules which additionally comprise povidone and magnesium stearate.

4. The composition according to claim 3 wherein the extended release layer further comprises sodium stearyl fumarate, or magnesium stearate; colloidal silicon dioxide; and microcrystalline cellulose.

5. A process for preparing a solid oral fixed dose composition according to claim 1 comprising forming a compressed bilayer part comprising:
    a. an extended release layer comprising metformin, or a pharmaceutically acceptable salt thereof, and one or more excipients; and
    b. an immediate release layer comprising valsartan, or a pharmaceutically acceptable salt thereof, and one or more excipients;
    and coating with an immediate release coating layer comprising atorvastatin, or a pharmaceutically acceptable salt thereof, and one or more excipients.

6. The process according to claim 5 wherein the immediate release coating layer comprising atorvastatin, or a pharmaceutically acceptable salt thereof, has a pH at or above 6.

* * * * *

UNITED STATES PATENT AND TRADEMARK OFFICE
CERTIFICATE OF CORRECTION

PATENT NO. : 11,376,223 B2
APPLICATION NO. : 16/628101
DATED : July 5, 2022
INVENTOR(S) : Matthew Carl Allgeier et al.

It is certified that error appears in the above-identified patent and that said Letters Patent is hereby corrected as shown below:

In the Claims
Column 15, Lines 24-25: In Claim 1, delete "fixed dose composition comprising a bilayer tablet comprising" and insert --fixed dose tablet composition comprising a bilayer part comprising--.
Column 15, Line 28: In Claim 1, delete "excipients; and" and insert --excipients;--.
Column 15, Line 36: In Claim 1, delete "tablet" and insert --tablet part--.
Column 16, Line 32-33: In Claim 5, delete "atorvastatin, or a pharmaceutically acceptable salt thereof," and insert --atorvastatin calcium trihydrate,--.
Column 16, Line 35-36: In Claim 6, delete "atorvastatin, or a pharmaceutically acceptable salt thereof," and insert --atorvastatin calcium trihydrate,--.

Signed and Sealed this
Sixth Day of December, 2022

Katherine Kelly Vidal
*Director of the United States Patent and Trademark Office*